United States Patent [19]

van der Laarse

[11] Patent Number: Plant 5,696

[45] Date of Patent: Mar. 18, 1986

[54] ANTHURIUM PLANT NAMED AMAZONE

[75] Inventor: Dirk van der Laarse, Aalsmeer, Netherlands

[73] Assignee: Anthurium Amazone Limited, Guernsey, Channel Islands

[21] Appl. No.: 613,407

[22] Filed: May 24, 1984

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Schwartz, Jeffery, Schwaab, Mack, Blumenthal & Evans

[57] ABSTRACT

A new and distinct anthurium plant named Amazone characterized by its long and relatively narrow leaves, generally round and very large spathes, red in color, carried on long stalks, and by its spadix which initially are curled and thereafter become generally straight and relatively long.

3 Drawing Figures

1

The present invention comprises a new and distinct cultivar of anthurium, botanically known as *Anthurium scherzerianum,* and hereinafter referred to by the cultivar name Amazone.

The new cultivar is a product of a planned breeding program, and was originated from a cross made during such a program in Aalsmeer, Netherlands in 1976. The male and female parents are unknown at this time. Amazone was discovered and selected as a flowering plant within the progeny of the parental cross by Dirk van der Laarse in a controlled environment in Aalsmeer, Netherlands. Subsequent asexual reproduction has demonstrated that the combination of characteristics as herein disclosed for the new cultivar are firmly fixed and are retained through successive generations of asexual reproduction.

The following traits have been repeatedly observed and in combination distinguish Amazone as a new and distinct cultivar:

1. Long and relatively narrow leaves, terminating in pointed ends which are frequently bent down.
2. Plant is medium large and relatively bushy.
3. The spathes are carried on very long stalks, which vary in color from medium to dark brown at bottom to a red color near the spathes.
4. The spathes are very large in size, generally elliptical to round in shape when viewed from the front, with a sinus formed between the top of the lobes, and generally half egg-shaped in cross-section.
5. The spathes are bright red in color, and very shiny when new, become somewhat more dull when older.
6. The spadix carried on the rim of the sinus is initially curled and then straightens out to a length of approximately 10 cm. The spadix is orange-red in color, with yellow markings.

7 The plant is continuously flowering.

The accompanying photographic drawings show typical foliage, spathe, and spadix characteristics of Amazone, with the colors being as nearly true as possible with illustrations of this type. Sheet 1 is a front perspective view of the entire plant. Sheet 2 contains two photographs, the upper one of which is a close up view of adjacent spathes and particularly showing the spadix shape and color, and the bottom one of which is a close up view of the reverse side of the spathe and the needle point at the bottom thereof.

The following observations, measurements and values describe plants grown in Aalsmeer, Netherlands

2 under greenhouse conditions which closely approximate those generally used in horticultural practice. The particular plant described is two (2) years old, and was developed from tissue culture. Color references are made to The Royal Horticultural Society (R.H.S.) Colour Chart, except where general color terms of ordinary significance are used.

Classification:

*Botanical.*—*Anthurium scherzerianum,* cv Amazone.

*Commercial.*—Anthurium.

Parentage: Unknown.

Propagation: At the present time, propagation is by tissue culture.

Plant: From 30 cm. to 40 cm. tall, and approximately 50 cm. in diameter when fully grown.

Leaves:

*Form and size.*—Relatively long and narrow, with the length up to 25 cm. and the width up to 9 cm. when fully grown; terminates in a sharp pointed end, which is generally bent downwardly; carried on stems up to 12 cm. in length.

*Texture.*—Slightly leathery in feel, medium shiny in appearance.

*Color.*—Upper side dark green, under side light to medium green; stems somewhat lighter green than upper side of leaf.

Spathe:

*Size.*—Very large, up to 18 cm. in length (vertical orientation) and approximately 14 cm. in width.

*Color.*—Upper side red 44A when new, darkening to 44A–45A on aging; underside slightly lighter than upper side.

*Arrangement.*—Carried on tall stalks medium to dark brown to red (at top) in color.

*Shape.*—Generally elliptical to round in front view, with greatest width dimension appearing midway above juncture with stem; approximately thirteen (13) parallel and longitudinal veins; sinus formed at juncture of top lobes.

*Texture.*—Upper side medium to highly shining, dulling with age; similar shine characteristic on underside.

Spadix: Sunken down on rim of sinus when opening, and curled; unfurling to a generally straight shape up to 10 cm. long; fairly coarse grained and orange red in color, with a multitude of yellow markings on surface.

Disease resistance: Very resistant to date to all diseases to which the variety is susceptible.

General observations: The new cultivar is unique by virtue of its very large and bright red spathes, each of which is carried on very tall stalks to produce a plant in which the flowering is positioned well above the leaves. The spadix is orange-red in color and curled when initially formed, opening to a relatively straight shape and relatively long.

I claim:

1. A new and distinct anthurium plant named Amazone, as described and illustrated, particularly characterized by its long and relatively narrow leaves, generally round and very large spathes, red in color, carried on long stalks, and by its spadix which initially are curled and thereafter become generally straight and relatively long, and further characterized by continuously flowering.

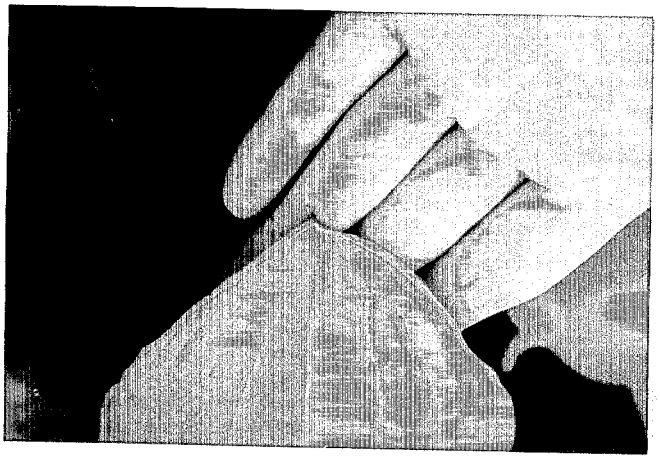
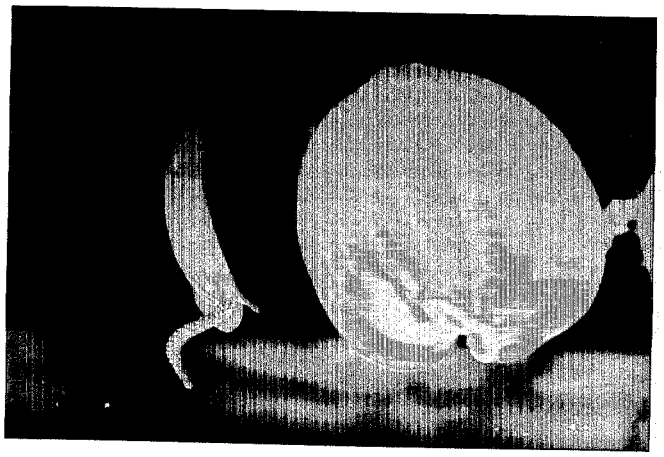

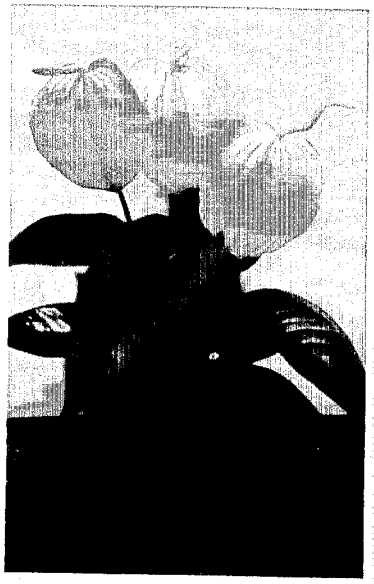

* * * * *